(12) United States Patent
Patil et al.

(10) Patent No.: US 7,518,005 B2
(45) Date of Patent: Apr. 14, 2009

(54) WATER-SOLUBLE ANTI-DANDRUFF COMPOUNDS AND COMPOSITIONS THEREOF

(75) Inventors: Sudhir Patil, Maharashtra (IN); Dilip Mhatre, Maharashtra (IN); Avila D'Souza, Maharashtra (IN)

(73) Assignee: Galaxy Surfactants Limited, Maharashtra (IN)

( * ) Notice: Subject to any disclaimer, the term of this patent is extended or adjusted under 35 U.S.C. 154(b) by 124 days.

(21) Appl. No.: 11/226,791

(22) Filed: Sep. 14, 2005

(65) Prior Publication Data

US 2006/0182696 A1  Aug. 17, 2006

(51) Int. Cl.
*C07C 233/00* (2006.01)
*C07C 231/00* (2006.01)

(52) U.S. Cl. .......................... 554/52; 424/59; 424/70.28

(58) Field of Classification Search ................ 554/68, 554/69, 52; 424/59, 70.28
See application file for complete search history.

*Primary Examiner*—Deborah D. Carr
(74) *Attorney, Agent, or Firm*—Akerman Senterfitt; Gregory A. Nelson; Gregory M. Lefkowitz

(57) ABSTRACT

Water-soluble and water dispersible undecylenic amido propyl dimethyl hydroxyl ethoxy ethyl ammonium undecylenate compounds of formula I having anti-dandruff, preservative and sunscreen activity wherein R1, R2 are from C1-C6 carbon atoms, R3 is undecylenic acid, amino group is selected from dimethyl amino propyl amine. Personal care compositions comprising compounds of formula I

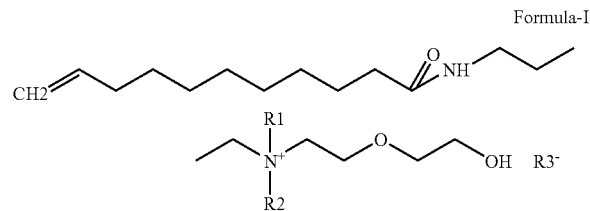

Formula-I

13 Claims, No Drawings

WATER-SOLUBLE ANTI-DANDRUFF COMPOUNDS AND COMPOSITIONS THEREOF

BACKGROUND OF THE INVENTION

1. Field of Invention

The present invention relates to water-soluble and water dispersible UV absorbing compounds and substantive anti-dandruff compounds and compositions thereof. The invention particularly relates to anti-dandruff and UV absorbing quaternary salts of Undecylenicamidoalkyl amine of Formula I,

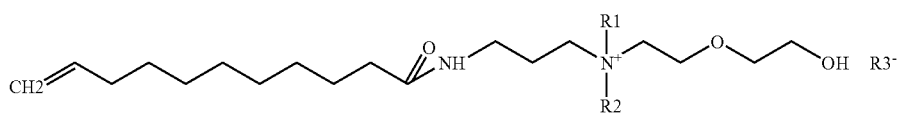

Formula I wherein

R1, R2 are from C1-C6 carbon atoms,

R3 is undecylenic acid, amino group selected from dimethyl amino propyl amine, which are substantive to skin, hair and fabric.

The present invention also relates to a process of preparation of these compounds and to the use of these compounds, in hair care, skincare & fabric care compositions.

2. Prior Art

It is known in art that many surfactants and additives used in shampoo products cause irritation to the eyes, which is of particular concern in shampoos used on infants and children. Accordingly attempts are made in prior art to develop surfactants and additives that are less irritating in nature.

It is observed that as children approach the age of puberty, hormonal changes associated with the development of scalp conditions normally associated with dandruff, such as scalp irritation and scaling, often occur. Incorporation of anti-dandruff agents thus becomes essential in hair care products for the treatment of the infected scalp.

For example, Undecylenic acid, which is commercially available, is used as an anti-dandruff agent in shampoos however it is a primary irritant and toxic substance.

Other known anti-dandruff molecules reported in Chemical products Desk reference compiled by Michael & Irene Ash.—that are based on Undecylenic acid are Undecylenamide DEA (CTFA) CAS # 25377-64-1; 60239-68-1, Undeylenamide MEA (CTFA) CAS # 20545-92-0; 25377-63-3, Undecylenamidopropyl trimonium methosufate, Undecylenic quat ammonium methosulfate, Undecylenic sulfosuccinate.

U.S. Pat. No. 4,307,089 discloses a cosmetic formulation consists of pyrithione compound in combination with undecylenic acid monoalkylolamide sulfosuccinate half ester for treatment of dandruff.

U.S. Pat. No. 3,385,755 discloses antibacterial and antifungal agents derived from Undecylenic acid alkylolamide and its derivative like undecylenic acid monoalkylolamide sulfosuccinate half ester.

U.S. Pat. No. 6,333,027 discloses a composition to treat dandruff in which Undecylenic amidopropyl betain is one of the active ingredients.

However these agents and compositions have found to be less effective against dandruff and there exists a need in the art to have a superior anti-dandruff agent that gives a long lasting protection against dandruff.

Other reported anti-dandruff products like ZPTO, Ketoconazole are either water-soluble or oil soluble. It is difficult to have clear shampoos with ZPTO and generally settling at the bottom is observed. Ketaconazole also requires additives for improving its solubility in formulations.

Therefore, there is a need for more effective anti-dandruff compounds, which has low degree of eye and skin irritation; effectively treat dandruff, and have superior physical characteristics that enable them to be easily formulated in hair care products.

The present inventors have surprisingly found that quaternary ammonium salts having two undecylenic acid moieties not only have more superior anti-dandruff activity compared to prior art compounds but also have dual water and oil solubility and are less irritant and are non-toxic.

OBJECTS OF THE INVENTION

It is thus the object of the present invention to provide water-soluble and water dispersible UV absorbing compounds and substantive anti-dandruff compounds that overcome the problems associated with prior art.

Another object of the present invention is to provide water-soluble and water dispersible UV absorbing compounds and substantive anti-dandruff compounds that are highly effective and have less irritancy and are non-toxic.

Another object of the present invention is to provide water-soluble and water dispersible UV absorbing compounds and substantive anti-dandruff compounds that are cheaper and can be easily formulated as hair care products.

Another object of the present invention is to provide anti-dandruff and UV absorbing quaternary salts of Undecylenicamidoalkyl amine that have two undecylenic acid moieties.

Yet another object of the present invention is to provide a process for the preparation of the water-soluble and water dispersible compounds and substantive anti-dandruff compounds.

Yet Another object of the present invention is to provide hair care compositions containing the water-soluble and water dispersible UV absorbing compounds and substantive anti-dandruff compounds.

Yet Another object of the present invention is to provide method of treating the dandruff infected scalp with the hair care compositions having the water-soluble and water dispersible UV absorbing compounds and substantive anti-dandruff compounds.

SUMMARY OF THE INVENTION

Thus according to an aspect of the present invention there are provided water-soluble and water dispersible undecylenic amido propyl dimethyl hydroxyl ethoxy ethyl ammonium undecylenate—compounds of formula I,

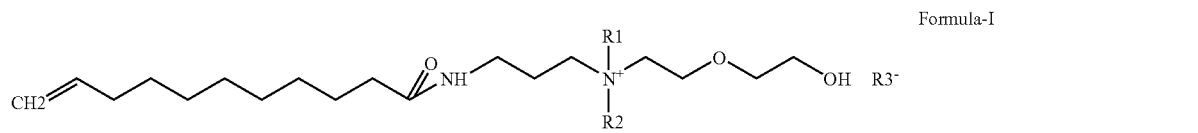

Formula-I wherein
R1, R2 from C1-C6 carbon atoms
R3 is undecylenic acid,
amino group is selected from dimethyl amino propyl amine According to a preferred aspect of the present invention there are provided water-soluble and water dispersible— compounds of formula I, wherein R1 and R2 are methyl groups and R3 is undecylenic acid According to another aspect of the present invention, there is a provided a process for the preparation of the compounds of Formula-I comprising the following steps Step I:—Amide Formation

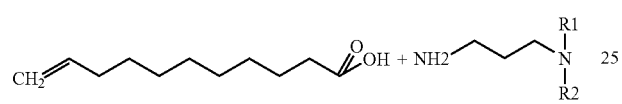

-continued

Undecylenic acid is reacted with dimethylamino propyl amine at 130-195 deg cent. Reaction is monitored by free undecylenic acid & amine value. Reaction is stopped when free undecylenic acid is less than 5%.

Step-II:—Ethoxylation.

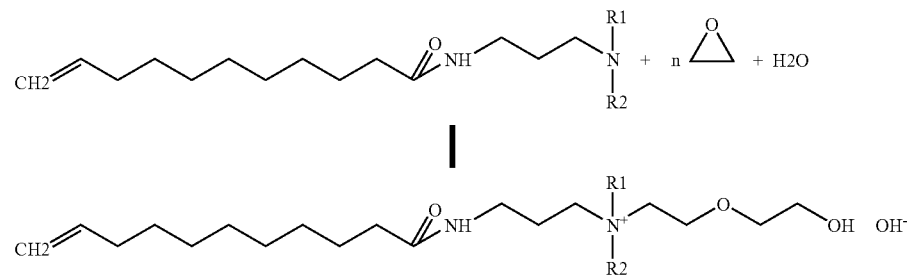

Reaction is carried out at 0-80 deg cent. Reaction is monitored by free amide content. When free amide is less than 0.2%, reaction is stopped.

Step-III:—Neutralization

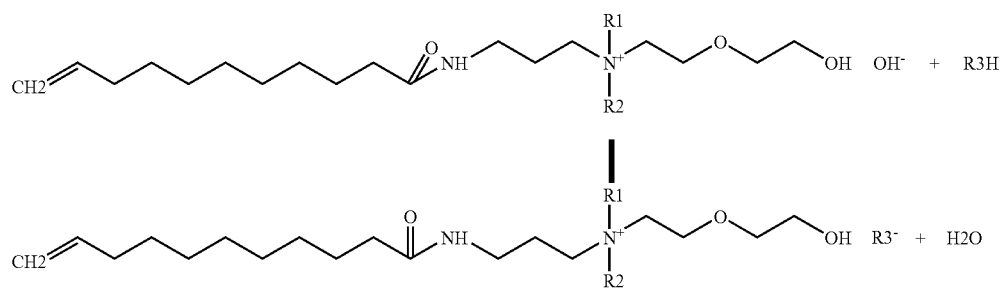

where R3H Undecylenic acid.

It is simple neutralization reaction. Step-II product was neutralized with undecylenic acid at 10-80 deg cent. Reaction is monitored by free undecylenic acid content. Free undecylenic acid should be less than 3%.

According to a third aspect of the present invention there are provided personal care compositions comprising compounds of Formula-I.

According to another aspect of the present invention, there is provided method of treating the dandruff infection with the personal care compositions containing compounds of formula-I comprising of topical application of an effective amount of the personal care compositions.

DETAILED DESCRIPTION OF INVENTION

The present inventors have identified derivatives of undecylenic acid that comprise undecylenic acid moieties have not only superior anti-dandruff properties but also provide attributes like viscosity boosting, preservative and conditioning properties care compositions.

These derivatives are both oil and water-soluble and hence can be easily formulated.

Personal care compositions can be formulated containing compounds of Formula-I in suitable quantities. More specifically the compositions comprise undecylenic amido propyl dimethyl hydroxyl ethyl ammonium undecylenate as a suitable anti-dandruff compound.

Personal care compositions of the present invention preferably comprise:
from 1 to 3% anti-dandruff compounds of Formula-I
from about 0% to 15% of at least one amphoteric surfactant
from about 8 to 14% anionic surfactant.
from about 0% to 5% of one non-ionic surfactant.

The amphoteric surfactant is any amphoteric compound, for example cocoamidopropyl betain. The anionic surfactant is any anionic compound like sodium lauryl ether sulfate, sodium lauryl sulfate. The non-ionic surfactant is any non-ionic compounds like fatty alcohol ethoxylate, Cocofatty acid ethanol amide, Cocofatty acid diethanol amide.

Undecylenic amido propyl dimethyl hydroxyl ethoxy ethyl ammonium undecylenate is formed reacting undecylenic acid with dimethyl amino proyl amine. The amide obtained is reacted with ethylene oxide in aqueous condition. After ethoxylation free alkalinity in the reaction is neutralized with undecylenic acid.

One or more ingredients selected from a group of active ingredients consisting of emulsifiers, thickening agents, skin and hair conditioning agents, humectants, surfactants, herbal extracts, emollients, rheological modifiers, other formulations excipients such as stabilizers, chelating agents, color, fragrance and median if any can also be incorporated in the compositions of the present invention.

The present invention also provides for the method of treating the disease of dandruff and symptoms associated with it comprising of the topical application of an effective amount of the personal care composition.

In the formulation of personal care composition in general is moreover necessary to add preservative agents, which have the function of preserving the composition from contamination by microorganisms such as bacteria, yeast & fungi, which can cause infections in man. However, the disadvantage associated with the use of preservative agents is that for them to be efficacious they must often be utilized in concentrations, which are irritating or sensitizing for the tissue with which they come in contact.

Since the compounds of the present invention have a preservative activity, in addition to their anti-dandruff activity in the concentrations used in the personal care compositions, this obviates the need to add preservatives separately hence is more beneficial than conventional anti-dandruff compounds.

The present invention therefore has the purpose of providing a personal care composition provided with the functional properties indicated above which does not have the disadvantages associated with the conventional compounds.

The compositions of the present invention may also include one or more optional ingredients nonexclusively including one or more pearlescent or opacifying agent, a thickening agent, emulsifiers, secondary conditioners, humectants, skin and hair conditioning agents, humectants, surfactants, herbal extracts, emollients, rheological modifiers, other formulations excipients such as stabilizers, chelating agents and additives which enhance their appearance, feel and fragrance, such as colorants, fragrances, preservatives, pH adjusting agents and the like. The pH of the shampoo compositions of this invention preferably maintained in the range of from about 5 to about 7.5 more preferably from about 5.5 to about 7.0.

The surfactants are selected from the group consisting of anionic, cationic, amphoteric and nonionic surfactants, from about 0% to 15% or more amphoteric surfactants, from about 8 to 14% one ore more anionic surfactants and from about 0 to 5% one ore more non-ionic surfactants can be incorporated.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent is present in an amount, based upon the total weight of the composition, of from about 1 percent to about 10 percent, preferably from about 1.5 percent to about 7 percent and more preferably, from about 2 percent to about 5 percent. Examples of suitable pearlescent or opacifying agents include, but are not limited to mono or diesters of a) fatty acids having from about 16 to about 18 carbon atoms.

In a preferred embodiment, the pearlescent or opacifying agent is introduced to the shampoo composition as a preformed, stabilized aqueous dispersion, such as that commercially available in Galaxy Surfactants Ltd. With trade name Sparkle 670. This material is a combination of glycol distearate, laureth-4 and cocoamido propyl betain and preferably is in the weight percent ratio of from about 20 to 30, 2 to 10, 10 to 20 respectively.

Commercially available secondary conditioners such as silicones, which impart, additional attributes, such as gloss to the hair are suitable to use in this invention.

The silicone conditioner is present in an amount of about 0 to 3 percent.

Examples of suitable chelating agent include those, which are capable of protecting and preserving the compositions of this invention. Preferable chelating agent is di sodium EDTA more preferably is tetra sodium EDT. It is present in an amount based on the total weight of the composition from about 0.02 to 0.25 percent.

The above described shampoo composition may be prepared by combining the desired components in a suitable container and mixing them under ambient conditions in any conventional mixing means well known in the art, such as via mechanically stirred propeller, paddle and the like. Although the order of mixing is not critical, it is preferable to pre-blend certain components, such as the fragrance, and the non-ionic surfactants before adding such components into the main mixture.

The amount of said anti-dandruff compounds may vary from 1-3%, w/w. for shampoo compositions, 0.5%-3% w/w for hair conditioners and bathing bar.

Advantages of the Invention

The biggest advantage of the composition containing anti-dandruff compound of the present invention is that it has more anti-dandruff activity when compared with other similar anti-dandruff compounds of prior art especially when applied through rinse off preparations like shampoo.

The other advantage of the composition containing anti-dandruff compound of the present invention is that it has very good water solubility and hence can be blended with anionic, cationic, nonionic and amphoteric surfactants.

In addition anti-dandruff compound of the present invention has good oil solubility and can be used in anti-dandruff hair oil preparations which is not possible in case of other anti-dandruff compounds mentioned in the prior art.

The invention illustratively disclosed herein suitably may be practiced in the absence of any component, ingredient or step, which is not specifically disclosed herein. Several non-limiting examples are set forth below to further illustrate the nature of the invention and the manner of carrying it out.

EXAMPLES

Example-1

Preparation of Undecylenic Dimethyl amido propyl amine

A 5000 ml autoclave was charged with 1000 gm (1.0 mole) Undecylenic acid, Dimethylaminopropyl amine 565.4 gm (1.02 mole). Stirring was started. Nitrogen was purged for 5 min to remove dissolve oxygen from reaction mass. Material slowly heated to 120-180° C. preferably 140-170° C. Reaction is monitored by free fatty acid & free amine. When desired specification was achieved, reaction mass was cooled up to 30° C. The final Undecylenic dimethylaminopropylamide was pale yellow in color. It has a purity 96%.

Example-2

Preparation of Undecylenic amidopropyl dimethyl Hydroxy ethoxy ethyl ammonium hydroxide (quarternary ammonium compound) from Undecylenic amidopropyl dimethyl amine A 5000 ml autoclave was charged 970 gm (1.0 mole) Undecylenic amidopropyldimethylamine, Water 3521 gm (54.05 mole). Stirring was started. Nitrogen was purged for 15 min to remove dissolved oxygen from reaction mass. Finally 0.5 kg/cm2 pressure was applied, 286 gm (1.8 mole) Ethylene oxide was added by maintaining reaction temperature 10-80° C., preferably 40-60° C. After ethylene oxide addition, reaction mass was digested for two hrs at same temperature. Then reaction mass was cool 30° C. The final quaternary ammonium compound was yellow color low viscous clear liquid. Product has purity of 25%.

Quaternary ammonium compound obtained from example 2 was neutralized with various raw material having COOH, OH groups to study water solubility, surfactant & UV properties.

Example-3
Preparation of Undecylenic amidopropyl dimethyl Hydroxy ethoxy ethyl ammonium Undecylenate (UADHEEAU)

A 2000 ml four neck round bottom flask was charged with 835 gm 25% (1.0 mole) Undecylenic amidopropyl Hydroxy-ethyl dimethyl ammonium hydroxide, Undecylenic acid 139 gm (1.0 mole) Stirring was started & reaction temperature was maintained between 30-70 degree C. for two hrs. Then reaction mass was cooled to 30 degree C. The final product was yellow color mass. Product is completely water-soluble. Product has purity of 32% & pH 8.0

Primary Dermal Irritation, Cumulative Dermal Irritation and Lethal Dose 50 tests for Undecylenic amidopropyl dimethyl Hydroxy ethoxy ethyl ammonium Undecylenate (UADHEEAU)

The aforesaid tests are tabulated in below table-I

TABLE I

| Study code | Sample no | Details | Test | Study code | Tested for | Result | Remarks |
|---|---|---|---|---|---|---|---|
| NTC 1372 a | AS 395 | UADHEEAU | LD 50 | Gaitonde Committee | Albino Mice, Oral route | >5.0 ml/kg | As is greater then 5.0 ml per kg. (36.19% solids) On 100% solid basis = greater than 1.825 ml per kgs. SAFE for use |
| 1373 e | AS 396 A | Shampoo base blank | PDI | BIS 4011 | Hair care product (8% solution) | 0.583 | Mild irritant, SAFE for use |

TABLE I-continued

| Study code | Sample no | Details | Test | Study code | Tested for | Result | Remarks |
|---|---|---|---|---|---|---|---|
| 1374 e | AS 396 B | Shampoo base, +5% UADHEEAU | PDI | BIS 4011 | Hair care product (8% solution) | 0.50 | Mild irritant, SAFE for use |
| 1373 | AS 396 A | Shampoo base blank | CDI | BIS 13424 | Hair care product (8% solution) | 0.60 | Mild irritant, SAFE for use |
| 1374 | AS 396 B | Shampoo base, +5% UADHEEAU | CDI | BIS 13424 | Hair care product (8% solution) | 0.58 | Mild irritant, SAFE for use |
| 1388 e | AS 399 A | Coconut oil (CNO) | PDI | BIS 4011 | Applied directly on skin | 0.00 | Non-irritant, SAFE for use |
| 1389 e | AS 399 B | CNO + 4% UADHEEAU | PDI | BIS 4011 | Applied directly on skin | 0.25 | Negligible irritant, SAFE for use |
| 1390 e | AS 399 C | CNO + 2% UADHEEAU | PDI | BIS 4011 | Applied directly on skin | 0.00 | Negligible irritant, SAFE for use |
| 1410 e | AS 3158A | CNO blank | PDI | BIS 4011 | Skin. Applied as such | 0 | Non irritant SAFE for use |
| 1411 e | AS 3158 B | CNO + 5% UADHEEAU | PDI | BIS 4011 | Skin. Applied as such | 0.417 | Negligible irritant SAFE for use |
| 1410 | AS 3158 A | CNO blank | CDI | BIS 13424 | Skin. Applied as such | 0.75 | Mild irritant, passed the test SAFE for use |
| 1411 | AS 3158 B | CNO + 5% UADHEEAU | CDI | BIS 13424 | Skin. Applied as such | 0.917 | Mild irritant, passed the test SAFE for use |

PDI = Primary Dermal Irritation

CDI = Cumulative Dermal Irritation

LD 50 = Lethal Dose 50

CNO = Coconut oil

Thus it can be interpreted from above table that undecylenic amidopropyl dimethyl hydroxy ethoxy ethyl ammonium undecylenate, an anti-dandruff compounds of formula-I of the present invention can be safely used in hair care shampoos. Leave on application with CNO is also safe.

Example-5

Comparison of Anti-Microbial Activity of Undecylenic amidopropyl dimethyl Hydroxy ethoxy ethyl ammonium Undecylenate Against M. furfur with Other Known Anti-Dandruff Agents M. furfur is one of the microorganism, which causes dandruff Method of Analysis: Zone of Inhibition Principle: Larger the zone of inhibition greater is the anti-dandruff activity.

TABLE 2

| Product | Concent. in % | Zone of inhibition in mm | Comments |
|---|---|---|---|
| Undecylenic amidopropyl dimethyl Hydroxy ethoxy ethyl ammonium Undecylenate (UADHEEAU) | 0.5 | 8 | Effective |
| | 1 | 11 | Effective |
| | 1.5 | 13 | Effective |
| | 2 | 13 | Effective |
| Undecylenic monoethanol amido sulfosuccinate | 0.5 | 0 | Not effective |
| | 1 | 0 | Not effective |
| | 1.5 | 0 | Not effective |
| | 2 | 0 | Not effective |
| Undecylenic mono ethanolamide | 0.5 | 0 | Not effective |
| | 1 | 2 | Less Effective |
| | 1.5 | 4 | Less Effective |
| | 2 | 6 | Less Effective |
| Undecylenic amidopropyl dimethyl Hydroxy ethyl ammonium chloride | 0.5 | 2 | Less Effective |
| | 1 | 3 | Less Effective |
| | 1.5 | 6 | Less Effective |
| | 2 | 8 | Effective |

Thus a comparison of prior art molecules with UADHEEAU in a concentration range of 0-2% effectively demonstrates the superior anti-dandruff activity of UADHEEAU.

Example 6

Comparison of Undecylenic amidopropyl dimethyl Hydroxy ethoxy ethyl ammonium undecylenate and ZPTO in SLES (Activity @ 14%)

Anti-microbial activity against M. furfur was studied for Undecylenic amidopropyl dimethyl Hydroxy ethoxy ethyl ammonium undecylenate at various concentration (1% to 2%) in SLES and were compared with 1% ZPTO.

TABLE 3

| Product | Concentration in % | Zone of inhibition in mm | Comments |
|---|---|---|---|
| Undecylenic amidopropyl dimethyl Hydroxy ethoxy ethyl ammonium undecylenate | 2% in SLES | 14 | Effective |
| | 1% in SLES | 12 | Effective |
| | 0.5% in SLES | 10 | Effective |
| | 2% in shampoo | 15 | Effective |
| | 1% in shampoo | 12 | Effective |
| | 0.5% in shampoo | 10 | Effective |
| ZPTO (Developed in self R&D lab.) | 1% in SLES | 14 | Effective |
| | 0.5% in SLES | 12 | Effective |
| | 1% in shampoo | 15 | Effective |
| | 0.5% in shampoo | 15 | Effective |

Above data shows that the present invented product Undecylenic amidopropyl dimethyl Hydroxy ethoxy ethyl ammonium Undecylenate is more effective than the other known anti-dandruff molecules.

Remarks 1.3-1.6% Undecylenic amidopropyl dimethyl Hydroxy ethoxy ethyl ammonium undecylenate is comparable with 1% ZPTO.

Example 7

Comparison of Undecylenic amidopropyl dimethyl Hydroxy ethoxy ethyl ammonium undecylenate with Undecylenic amido propyl betain Undecylenic amido propyl betain is a reported anti-dandruff product, so Undecylenic amidopropyl dimethyl Hydroxy ethyl ammonium undecylenate was compared. Carried out of zone of inhibition of M. furfur against 1, 2%, 5% & 7% Undecylenic amido propyl betain in SLES and compared it with Undecylenic amido propyl dimethyl Hydroxy ethyl ammonium undecylenate

TABLE 4

| Product | Concentration in % | Zone of inhibition in mm | Comments |
|---|---|---|---|
| Undecylenic amidopropyl betaine | 1% | 3 | Less effective |
| | 2% | 6 | Less effective |
| | 5% | 6 | Less effective |
| | 7% | 8 | Effective |
| Undecylenic amidopropyl dimethyl Hydroxy ethoxy ethyl ammonium undecylenate | 1% | 13 | Effective |
| | 2% | 16 | Effective |

Result:

1% Undecylenic amidopropyl dimethyl Hydroxy ethoxy ethyl ammonium undecylenate is found to be effective than 7% Undecylenic amido propyl betain.

Example 15

Challenge Test of Shampoo Formulation

Challenge test of shampoo formulation with Yeast and fungus was carried out to find the preservative efficacy of the product.

TABLE 4

| | Microbial count CFU/ml | | | | |
|---|---|---|---|---|---|
| Micro-organism | 0 hrs | 24 hrs | 7 days | 14 days | 21 days | 28 days |
| Candida albicans ATCC 10231 | $1.02 \times 10^6$ | $6 \times 10^3$ | <10 | <10 | <10 | <10 |
| Aspergillus niger ATCC 16404 | $3.6 \times 10^5$ | $1.3 \times 10^5$ | $3.8 \times 10^5$ | — | — | $1.5 \times 10^5$ |

It can be concluded from the data the compounds of the present invention are very effective against yeast whereas it acts as fungi static against fungus.

Example 8

Minimum Inhibitory Concentration (MIC)

The minimum inhibitory concentration (MIC) of the product was carried out by broth dilution method. The MIC values are as follows:

TABLE 5

| Microorganism | MIC in PPM on 100% solids basis |
|---|---|
| Staphylococcus aureus ATCC 6538 | 204-320 |
| Escherichia coli ATCC 10148 | 883-1080 |
| Pseudomonas aeruginosa Immunotype IV | 1697-1800 |
| Candida albicans ATCC 10231 | 50-250 |
| Aspergillus niger ATCC 16404 | 30-160 |

Lesser the MIC value greater is the anti-microbial activity.

Example 9

To Demonstrate Viscosity Booster Effect

Undecylenic amidopropyl dimethyl Hydroxy ethoxy ethyl ammonium undecylenate can also be used as an Viscosity booster in a shampoo formulation. Viscosity profile of a shampoo formulation using cocomonoethanalomide and Undecylenic amidopropyl dimethyl Hydroxy ethoxy ethyl ammonium undecylenate is as follows Cocomonoethanolamide is available from Galaxy Surfactants Ltd. as Galaxy 100.

Formulations include 15% active sodium lauryl ether sulfate, cocomonoethanalomide or Undeylenic amidopropyl dimethyl Hydroxy ethoxy ethyl ammonium undecylenate 2%, sodium chloride at Various concentration level and water sufficient to make 100 percent.

TABLE 6

| | Viscosity in cps at 28° C. | | |
|---|---|---|---|
| Concentration of Sodium chloride in % | Control without viscosity booster | CMEA | Undecylenic amidopropyl dimethyl Hydroxy ethoxy ethyl ammonium undecylenate |
| 0.5 | — | 55 | — |
| 1.0 | — | 600 | 3800 |
| 1.5 | 55 | 3000 | 7450 |
| 2.0 | 80 | 11000 | 10600 |
| 2.5 | 1100 | 17000 | 13000 |

Example 10

Preparation of Shampoo Formulations

Clear Shampoo:

| | |
|---|---|
| SLES 28% active | 14% |
| Cocomonoethanol amide | 2% |
| Cocoamidopropyl betain | 5% |
| UAPDHEEAU (37%) | 5-6% |
| Perfume | QS |
| Color | QS |
| Sodium chlorirde | 1.5% max. |
| Water | QS |

(B) Pearly Shampoo:

| | |
|---|---|
| SLES 28% active | 14% |
| Cocomonoethanol amide | 2% |
| Cocoamidopropyl betain | 5% |
| EGDS | 2% |
| UAPDHEEAU (37%) | 5-6% |
| Perfume | QS |
| Color | QS |
| Sodium chlorirde | 1.5% max. |
| Water | QS |

UAPDHEAU: - Undecylenic amidopropyl dimethyl hydroxyl ethoxy ethyl ammonium undecylenate.
EGDS: - Ethylene glycol distearate.

What is claimed is:

1. A water-soluble and water dispersible undecylenic amido propyl dimethyl hydroxyl ethoxy ethyl ammonium undecylenate compounds of formula-I Formula-I wherein
R1, R2 are from C1- C6 carbon atoms
R3 is undecylenic acid
the amino group is selected from dimethyl amino propyl amine.

2. A compound of formula-I wherein R1 and R2 are methyl groups

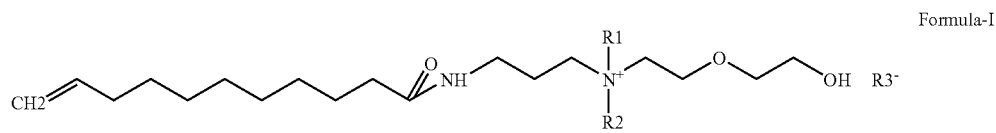
Formula-I wherein
R3 is undecylenic acid
the amino group is selected from dimethyl amino propyl amine.

3. A compound of formula-I having anti-dandruff, preservative, and sunscreen activity 9. The personal care as claimed in claim 4 comprising:
about 1-3% w/w of compounds of Formula-1 having R1 and R2 as methyl groups;
about 50% w/w of SLES (2 mole);
about 5% w/w of polyquaternium 7; and
about 5% w/w of cocoamidopropyl betain.

8. The personal care composition as claimed in claim 4 wherein said compound of formula I and other ingredients are water-soluble or water dispersible, and the said composition is an aqueous form.

10. The personal care compositions as claimed in claim 4 in the form of transparent bars comprising about 2% w/w of compounds of Formula-1 having R1 and R2 as methyl groups, about 25% w/w of SLES (2 mole), about 16% w/w of cocaamidopropyl betain, about 20%w/w of propylene glycol, about 9% w/w of sodium cocoate and about 14% w/w of sodium stearate.

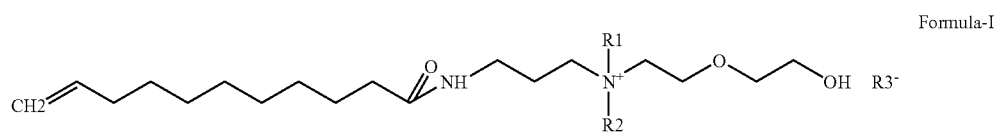
Formula-I wherein
R1, R2 are from C1- C6 carbon atoms
R3 is undecylenic acid
the amino group is selected from dimetihyl amino propyl amine.

4. A personal care composition comprising compounds of formula I as claimed in claim 1.

5. The personal care composition as claimed in claim 4 further comprising one or more ingredient selected from a group of active ingredients consisting of emulsifiers, thickening agents, skin and hair conditioning agents, humectants, surfactants, herbal extracts, emollients, and rheological modifiers.

6. The personal care composition as claimed in claim 4, in the form of a shampoo, hair conditioner, or bathing bar.

7. The personal care composition as claimed in claim 4 wherein the amount of said compound of formula I is from 0.5%-3% w/w.

11. The personal care compositions as claimed in claim 4 as leave on preparation wherein said anti-dandruff compound of Formula-I has R1 & R2 as methyl groups and present in amounts of about 1-4% w/w in coconut oil, with perfume 0.2-0.5% w/w, colour 0.02-0.05% w/w, and anti-oxidant 0.01-0.03% w/w.

12. A process for the preparation of the compounds of Formula-I comprising the steps of
a) reacting undecylenic acid with dimethyl amino proyl amine to form an amide;
b) the amide obtained is reacted with ethylene oxide under aqueous conditions; and
c) the alkalinity in the reaction mass is neutralized with undecylenic acid.

13. The personal care composition as claimed in claim 4, further comprising one or more ingredient selected from the group consisting of stabilizers, chelating agents, colors, and fragrances.

* * * * *

UNITED STATES PATENT AND TRADEMARK OFFICE
CERTIFICATE OF CORRECTION

Page 1 of 1

PATENT NO. : 7,518,005 B2
APPLICATION NO. : 11/226791
DATED : April 14, 2009
INVENTOR(S) : Patil et al.

It is certified that error appears in the above-identified patent and that said Letters Patent is hereby corrected as shown below:

Cover page, underneath the Prior Publication Data Section, please insert:

--(30) Foreign Application Priority Data

Feb. 14, 2005 (IN) ................ 156/MUM/2005--

Signed and Sealed this
Twenty-fifth Day of September, 2012

David J. Kappos
*Director of the United States Patent and Trademark Office*